United States Patent [19]

English et al.

[11] Patent Number: 5,149,505
[45] Date of Patent: Sep. 22, 1992

[54] DIAGNOSTIC TESTING DEVICE

[75] Inventors: Kenneth P. English, Bolingbrook; Stanley E. Micek, III, Grayslake; Michael B. O'Connell, Waukegan; Edward S. Tripp, Park City, all of Ill.

[73] Assignee: Abbott Laboratories, North Chicago, Ill.

[21] Appl. No.: 381,360

[22] Filed: Jul. 18, 1989

[51] Int. Cl.5 .................... B01L 3/00; G01N 21/01
[52] U.S. Cl. ........................ 422/99; 422/64; 422/68.1; 422/100; 422/58; 422/102; 436/808; 435/299; 435/300; 435/301
[58] Field of Search ............ 422/64, 68.1, 50, 61, 422/58, 102, 99, 100; 436/808; 435/809, 299, 300, 301, 973, 975; 222/187

[56] References Cited

U.S. PATENT DOCUMENTS

| | | | |
|---|---|---|---|
| 3,990,852 | 11/1976 | Piazzi et al. | 422/102 |
| 4,237,234 | 12/1980 | Meunier | 422/61 X |
| 4,241,188 | 12/1980 | Materia et al. | 422/102 X |
| 4,246,339 | 1/1981 | Cole et al. | 436/808 X |
| 4,260,687 | 4/1981 | Jacobson et al. | 435/301 |
| 4,348,207 | 9/1982 | Cappel | 422/102 X |
| 4,385,115 | 5/1983 | de Zabala et al. | 435/299 X |
| 4,643,974 | 2/1987 | Berretti et al. | 435/299 X |
| 4,703,864 | 11/1987 | Larkin et al. | 220/270 X |
| 4,822,571 | 4/1989 | Nicholson et al. | 422/265 X |
| 4,839,297 | 6/1989 | Freitag et al. | 422/58 X |
| 4,859,603 | 8/1989 | Dole et al. | 436/808 X |
| 4,943,522 | 7/1990 | Eisinger et al. | 422/58 X |
| 5,006,474 | 4/1991 | Horstman et al. | 422/61 X |

Primary Examiner—James C. Housel
Assistant Examiner—Arlen Soderquist
Attorney, Agent, or Firm—Priscilla E. Porembski; Daniel W. Collins; Thomas M. Breininger

[57] ABSTRACT

A diagnostic testing device is disclosed. The testing device includes a base member and a cover member which defines an opening for the reception of a liquid specimen. A distribution wheel delivers portions of the specimen to antibiotic units which are circumferentially spaced. Indicator units are in communication with the cover member. A delivery cylinder extends upwardly from each of the antibiotic units toward a respective one of the indicator units. Relative vertical movement between the delivery cylinder and the indicator unit places the cylinder and the indicator unit into an engaging relationship. A change in coloration at an indicator unit indicates a positive reaction.

27 Claims, 7 Drawing Sheets

DIAGNOSTIC TESTING DEVICE

BACKGROUND OF THE INVENTION

The present invention relates to a diagnostic testing device and more particularly to an antibiotic resistance test kit. Primary care physicians, such as family practitioners and physicians specializing in internal medicine, often prescribe a broad spectrum drug even though they are well aware that such drug over a period of time may produce a resistance or immunity in the patient.

Accordingly, there has been a need for a simple diagnostic testing device where a doctor is able to test, without requesting the services of an outside laboratory, and depending on the test results prescribe a specific antibiotic.

The primary purpose of the present invention is to provide a diagnostic testing device which may be utilized by a primary care physician or by other medical personnel without sending the testing device to an outside laboratory.

A further object of the present invention is to provide a diagnostic testing device which does not require the primary care physician to purchase extensive capital equipment and where the testing device has a relatively low-cost unit price.

Other objects of the invention will be apparent for the following specification and claims.

SUMMARY OF THE INVENTION

The present invention is directed to a diagnostic testing device having a base member which defines a cavity. A plurality of antibiotic units are positioned within the cavity. A cover member is located on the base member and defines a cover opening for the reception of a liquid specimen, such as a urine specimen.

A distribution system is positioned between the cover opening and the antibiotic units for delivering portions of the liquid specimen to each of such units.

Indicator means, which give either a positive or negative reading by a color change, are in communication with the cover member. A delivery member extends upwardly from each of the antibiotic units. A biasing means allows the cover member to stably achieve a first and second position relative to the central member whereby in the first position the delivery member and the indicator means are not in fluid communication with each other and in the second position the delivery member and the indicator means are in fluid communication with each other. Relative vertical movement between the delivery means and the indicator means places the delivery means and the indicator means into an engaging relationship. A color change normally indicates a positive response which indicates that there is a resistance to a particular antibiotic.

For reference purposes, throughout the following specification and claims, the term vertical is utilized in indicating movement and positioning. For example, the term vertical is used in connection with the base member and the cover where the base member is horizontally positioned and the cover is essentially parallel to the horizontal base member. However, it is understood that the base member and the cover may be rotated ninety degrees and the use of the terms "vertical", "upwardly" and "downwardly" are not meant to limit the scope of the present invention.

DESCRIPTION OF THE PREFERRED EMBODIMENTS

Figure 3:
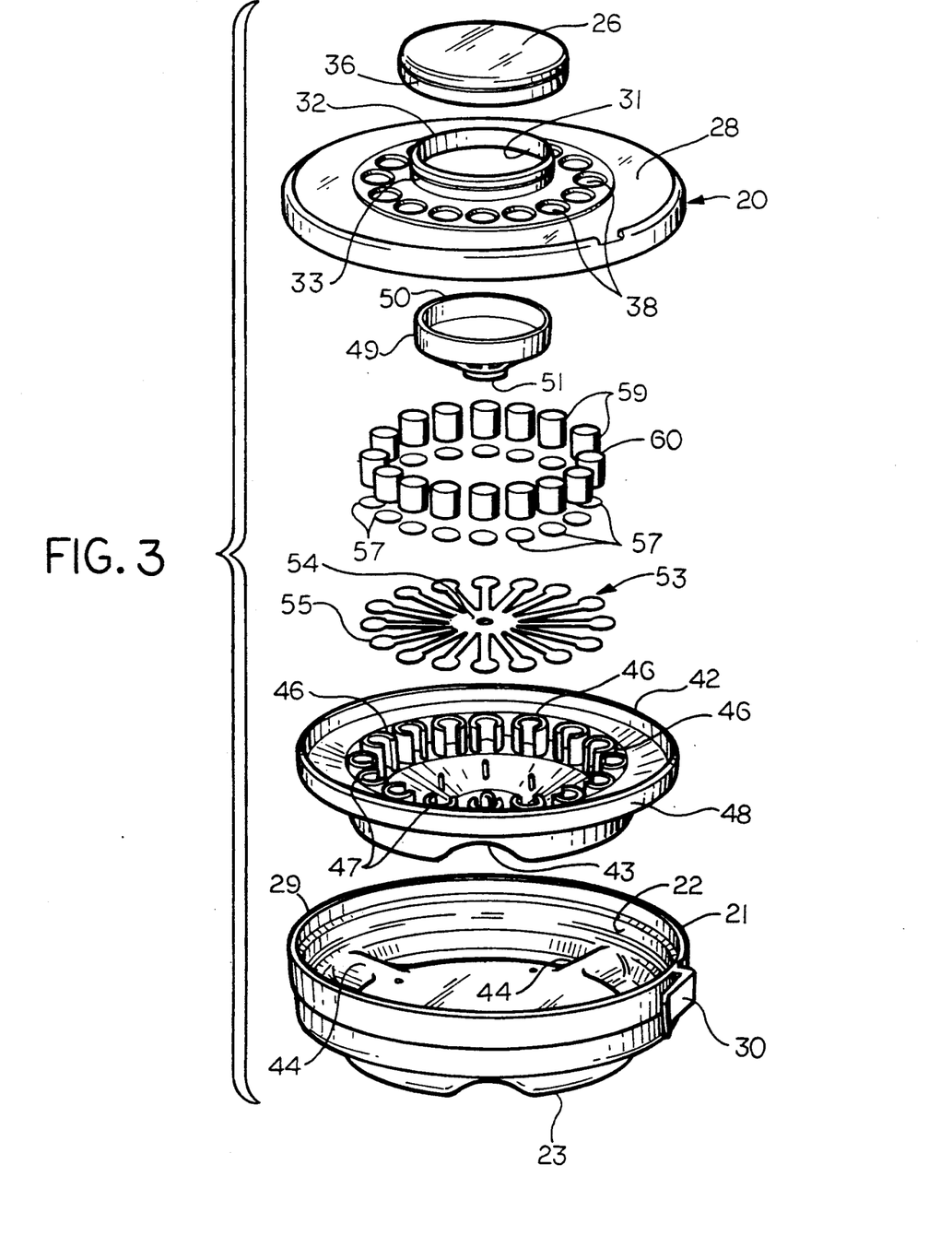
FIG. 3 is an exploded view of the various components of the diagnostic testing device shown in FIG. 1.
Figure 4:
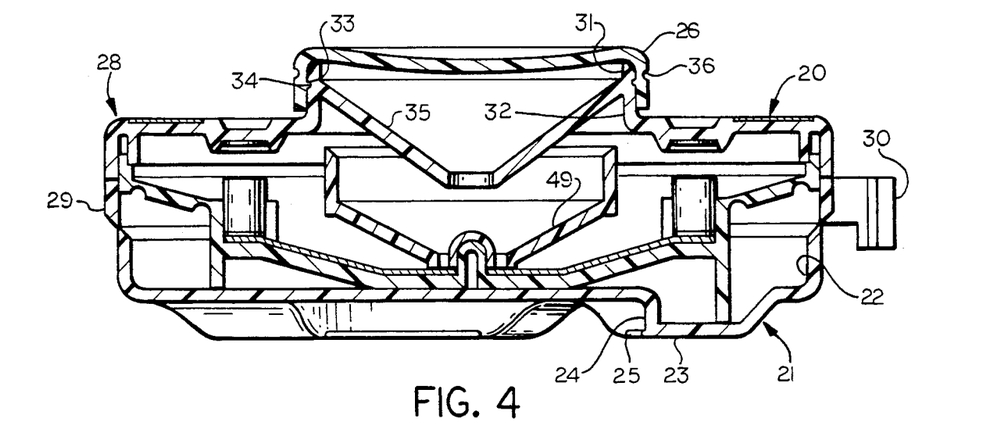
FIG. 4 is a sectional view, shown on an enlarged scale, taken along the line 4—4 of FIG. 1.

One embodiment of a diagnostic testing device, according to the present invention, is generally indicated in FIGS. 1 and 3–8 by the reference number 20. The testing device 20 includes a base member 21 which defines a cavity 22. In the present embodiment, the base member 21 and other components are constructed of plastic materials such as a polyethylene or a polypropylene, however, they may be constructed of other materials. The base member 21 has a lower surface 23 which defines a circular recess 24. In the present embodiment, the testing device 20 and the base member 21 are circular in configuration. It is understood that other configurations are possible and fall within the scope of the present invention. Referring to FIG. 4, the recess 24 has a circular ridge 25 which services as an initial retaining means for a cap 26, as discussed below.

Figure 1:
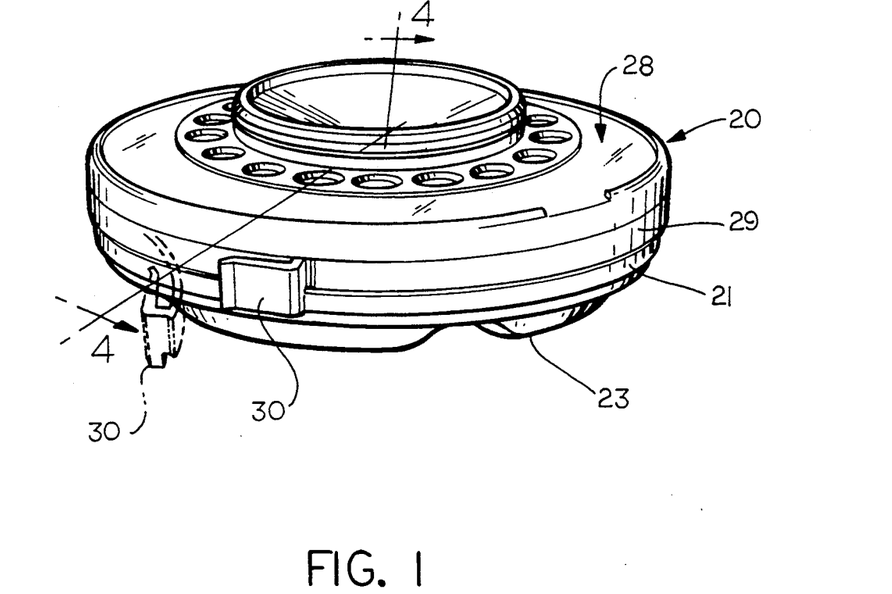
FIG. 1 is a perspective view of a diagnostic testing device, according to the present invention, with a tear strip tab being shown in dashed lines as it is being removed.
Figure 2:
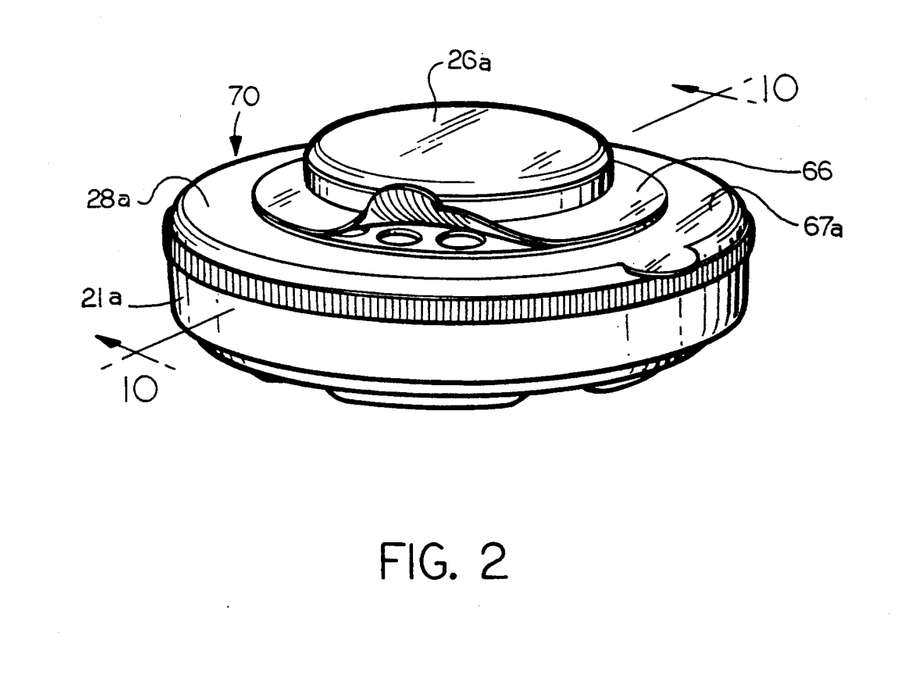
FIG. 2 is a perspective view similar to FIG. 1 showing another embodiment of a diagnostic testing device, according to the present invention and showing an inner label partially removed on the cover.

A cover member 28 is also circular in the present embodiment. It is constructed of similar material and is mounted on the base member 21. In the present embodiment, the base member 21 and cover member 28 are joined together by a tear strip 29 having a tear tab 30.

The cover member 28 defines a central opening 31 for the introduction of a liquid specimen, such as a urine specimen. A neck 32 extends upwardly from the cover member 28 and defines the opening 31 on its interior and a circular groove 33 on its exterior. The circular groove 33 mates with an interior ridge 34 defined on the interior of the cap 26. A throat section 35 extends downwardly from the neck 32. After a liquid specimen is introduced through the central opening 31, the cap 26 is removed from the recess 24 in the lower surface 23 of the base member 21 and snapped in place on the neck 32. The circular groove 33 and the cooperating cap ridge 34 serve as locking means for securing the cap 26 to the cover member 28. It should be understood that the locations of the groove and ridge 33-34 may be reversed without departing from the scope of the attached claims.

The exterior of the cap 26 defines a circular groove 36 which cooperates with the circular ridge 25 defined in the recess 24 of the base member 21. The securing of the ridge 25 to the cap groove 36 initially secures the cap 26 to the base member 21 prior to use of the diagnostic testing device 20.

In the present embodiment, the cover member 28 defines a plurality of circumferentially spaced indicator stations 38. Each indicator station 38 includes a transparent bottom 39. An indicator coating layer 40 is applied to the transparent bottom 39. In the present embodiment, the indicator coating layer is a tetrozolium indicator, however, other indicators may be used and still be within the scope of the present invention. If bacteria are present, when the bacteria engages the indicator coating 40, a positive reaction occurs and the color of the coating 40 changes. In the present embodiment, the indicator coating 40 changes to a purple color when a positive reaction occurs. If no bacteria are present, then the indicator coating 40 maintains its initial or neutral coloring.

In the present embodiment, referring to FIGS. 3-8, a circular central member 42 is positioned between the base member 21 and the cover member 28. The central member 42 defines a plurality of indexing grooves 43 on its lower surface which mate with raised indexing portions 44 defined in the base member 21. Integrally attached to the central member 42 are a plurality of circumferentially spaced antibiotic units 46. Each of the antibiotic units 46 comprises a generally cylindrical member having a slotted opening 47. The cylindrical members or antibiotic units 46 are spaced from the periphery 48 of the central member 42.

Distribution means are positioned between the central opening 31 of the cover member 28 and the antibiotic units 46 for delivering portions of the liquid specimen to such antibiotic units 46. In the device 20, the distribution means includes a funnel member 49 having an upper end 50 adjacent the throat section 35 depending from the central opening 31 of the cover member 28. The funnel member 49 has a lower end 51.

A distribution wheel 53 having a central portion 54 and a plurality of radially extending spokes or legs 55 is positioned in the central member 42 with the portion 54 being located adjacent the lower end 51 of the funnel member 49. The distribution wheel 53 has a snowflake configuration, as shown in FIG. 3, and is constructed of wicking material. The material is preferably a fibrous material. In the present embodiment it has been found that a material sold by Lydall Incorporated under the designation "LYDAIR No. 9254" works satisfactorily. The outer ends of the spokes or legs 55 extend through the slotted openings 47 and are positioned within the generally cylindrical antibiotic units 46. Antibiotic disks 57 are positioned in the antibiotic units 46 in contact with the outer ends of the legs 55 of the distribution wheel 53. In the present embodiments, the antibiotic disks 57 are antibiotic disks sold by Benton Dickenson, however, other antibiotic units may be utilized with diagnostic testing devices according to the invention.

The liquid specimen is discharged from the lower end 51 of the funnel member 49 onto the central portion 54 of the distribution wheel 53. By a wicking action the specimen is then distributed along the legs 55 to the antibiotic units 46 and into contact with the antibiotic disks 57.

A cylindrically shaped delivery member 59 has its lowermost end positioned within the one of the antibiotic units 46 adjacent one of the antibiotic disks 57. The delivery member 59 is constructed of wicking material in the shape of a cylinder. In this embodiment, the wicking material is a cellulose acetate material manufactured by American Filtrona. The Filtrona cylinder is sold under the mark "TRANSORB". It is understood that other materials may be utilized in connection with the present invention. The delivery member or fibrous member 59 which is positioned in the generally cylindrical antibiotic unit 56 extends upwardly toward the cover member 28. The delivery member 59 includes a upper end 60. In the present embodiment, relative vertical movement between the cylindrical delivery member 59 and the cover member 28 places the upper end 60 into engagement with the indicator coating layer 40 at a respective one of the indicator stations 38.

Referring to FIGS. 4-8, a hinge assembly 62 is positioned between the central member 42 and the cover member 28. The hinge assembly 62 comprises a living hinge having a first edge 63 integrally attached at the periphery of the central member 42 and its outermost edge 64 positioned adjacent the cover member 28.

During a typical operation of a diagnostic testing device 20, a urine specimen (see FIG. 5) is introduced through the central opening 31 downwardly into the throat 35 and the funnel member 49. The liquid specimen is discharged through the lower end 51 onto the distribution wheel 53. The specimen then wicks outwardly along the legs 55 to the respective antibiotic units 46.

Figure 5:
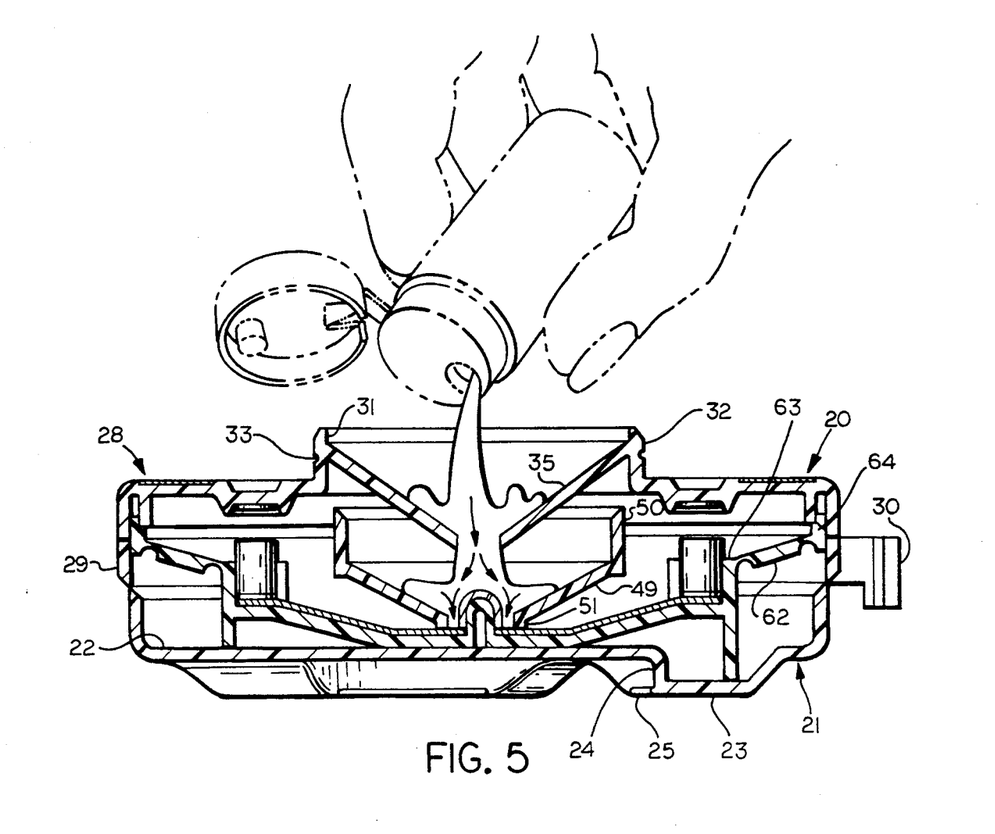
FIG. 5 is a cross-sectional view similar to FIG. 4 and showing the introduction of a liquid specimen into the diagnostic testing device.

The cap 26 is removed from the lower surface 23 of the base member 21 and snapped in place on the neck 32 of the cover member 28. From this time forward, the testing device 20 remains closed with its contents remaining isolated. At this time, the diagnostic testing device 20 is inverted and the device incubated for approximately three hours at 37° C.

Figure 6:
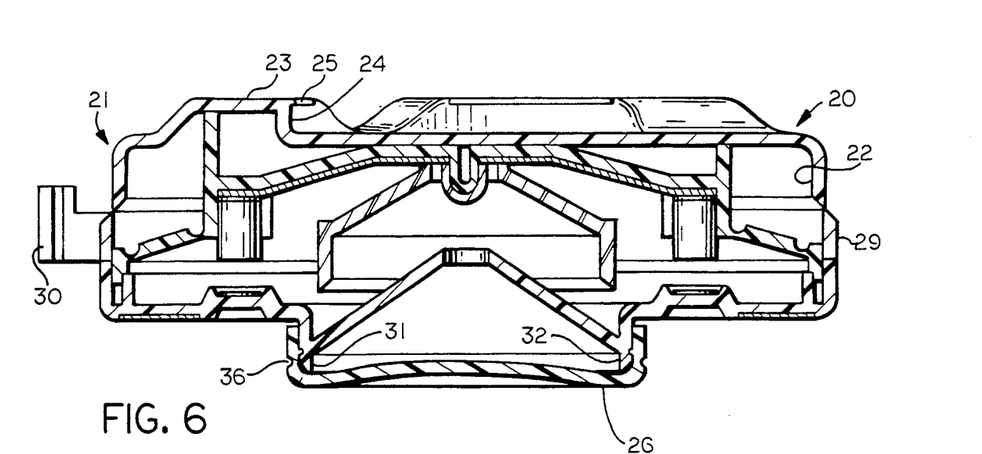
FIG. 6 is a view similar to FIG. 5 with the diagnostic testing device inverted.
Figure 7:
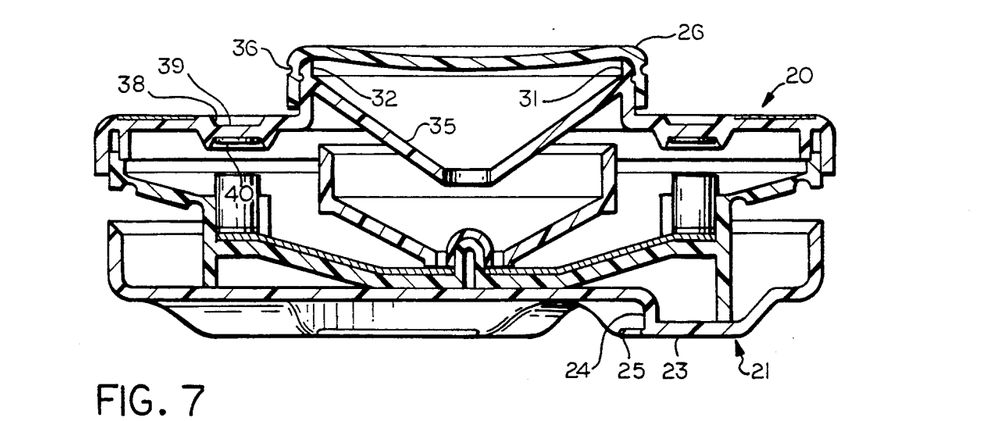
FIG. 7 is a sectional view similar to FIG. 6 with the tear strip removed.
Figure 8:
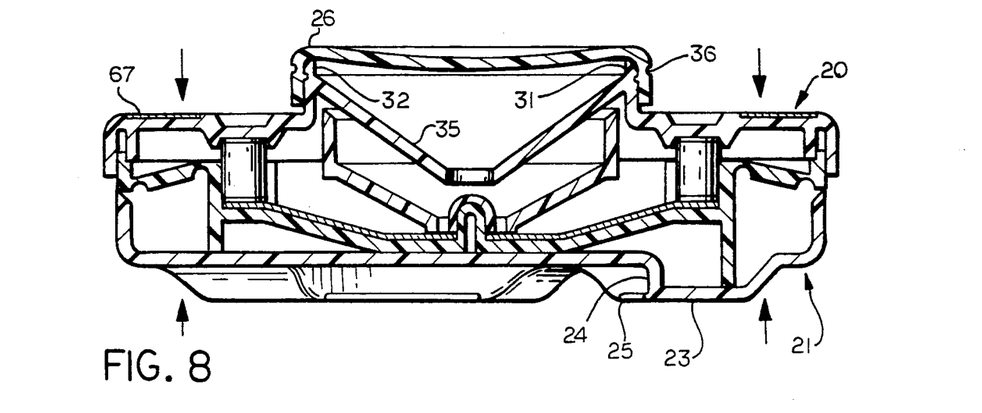
FIG. 8 is a sectional view similar to FIG. 7 after the testing device has been compressed.
Figure 9:
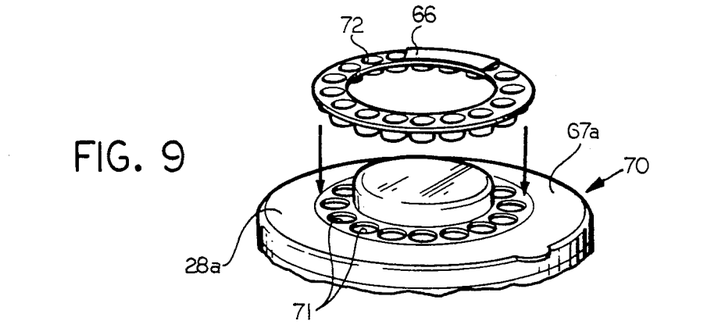
FIG. 9 is a fragmentary exploded view showing the positioning of a top indicator ring downwardly into the cover with respect to the embodiment shown in FIG. 2.

Referring to FIGS. 6-8, after incubation the operator grasps the tear tab 30 and removes the tear strip 29. Removal of the tear strip 29 allows relative movement between the base member 21 and the cover member 28. Referring to FIGS. 7 and 8, squeezing these two units together snaps the living hinge assembly 62 into the position shown in FIG. 8 where the cylindrical delivery members 59 are moved upwardly with their upper ends 60 engaging and remaining against the indicator coating layers 40 at the indicator stations 38. The diagnostic testing device 20 may be read in approximately fifteen minutes. As previously mentioned, a purple coloration indicates a positive reaction. Any positive reactions are noted on an outer circular label 67. The outer circular label 67 is correctly indexed with specific antibiotic disks so that the primary care physician can refer to the label which is removed and placed in the patient's file to prescribe a specific antibiotic rather than using a broad spectrum antibiotic.

It has been found that a diagnostic testing device 20, according to the present invention, is an efficient and relatively inexpensive way of providing superior treatment to patients by primary care physicians.

Another embodiment of a diagnostic testing device, according to the present invention, is generally indicated in FIGS. 2, 9, 10 and 11 by the reference number 70. The diagnostic testing device 70 includes a base member 21a and a cover member 28a. The base member 21a defines a cavity 22a which receives a circular central member 42a. A fibrous distribution wheel 53a is positioned on the upper surface of the central member 42a and a plurality of radially extending spokes or legs 55a extend outwardly with their ends terminating in respective ones of antibiotic units 46a. Antibiotic disks 57a are positioned in the antibiotic units 46a adjacent the outer ends of the legs 55a of the distribution wheel 53a. Cylindrically shaped delivery members 59a extend upwardly out of the antibiotic units 46a toward the cover member 28a. The cover member 28a of the diagnostic testing device 70 defines a plurality of circumferntially spaced indicator openings 71. The indicator means of the diagnostic testing device 70 includes a separate indicator ring 72 which has a plurality of indicator units 73 depending downwardly at spaced locations around the indicator ring 72. The bottoms of the indicator units 73 are transparent and include an indicator coating layer 74 on their lowermost surface.

Figure 10:
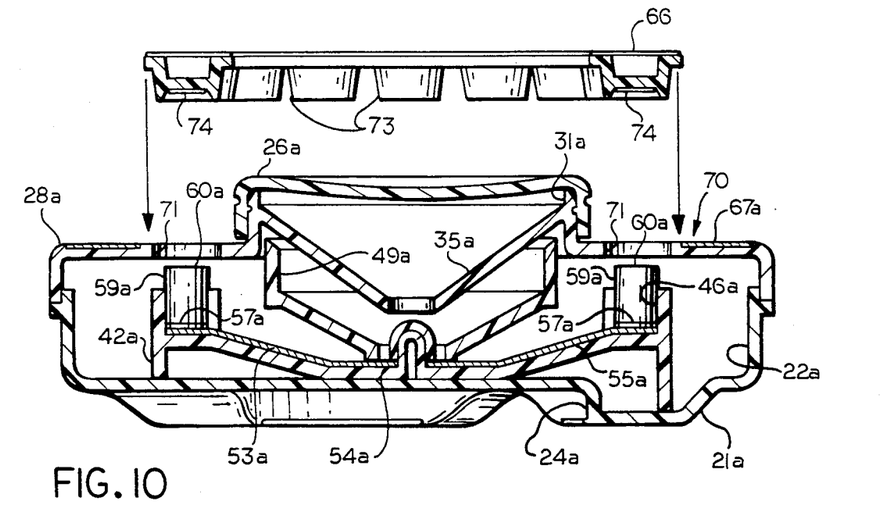
FIG. 10 is an enlarged sectional view taken through FIG. 2 and showing the top ring moving downwardly into position.
Figure 11:
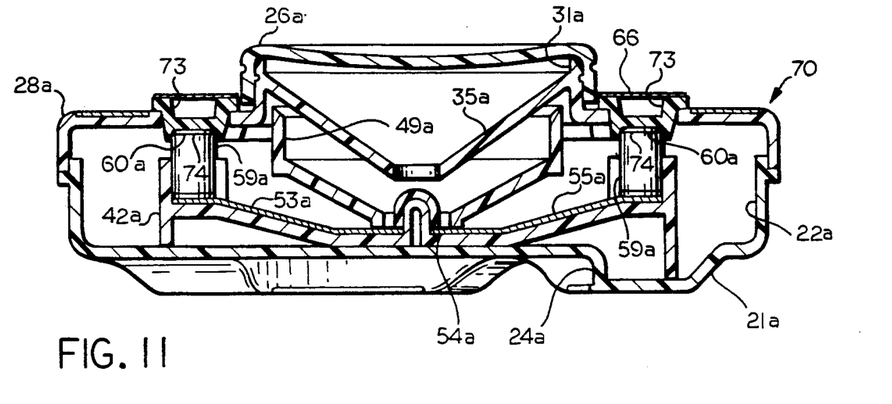
FIG. 11 is a cross-sectional view similar to FIG. 10 with the top ring in its down position.

Again, the diagnostic testing device 70 includes a cap 26a which is initially held in a circular recess 24a of the base member 21a. After the urine specimen is introduced in a central opening 31a of the cover member 28a, the cap 26a is repositioned and held in place as shown in FIGS. 10 and 11. A throat 35a and the supply tube or funnel member 49a directs the liquid specimen downwardly to the central portion 54a of the distribution wheel 53a. In this embodiment, the base member 21a and the cover member 28a are joined together. Relative vertical movement occurs by moving the indicator ring 72 downwardly so that the individual indicator units 73 are received in respective ones of the indictor openings 71 defined in the upper surface of the cover member 28a. When this relative vertical movement occurs, the upper ends 60a of the delivery cylinders 59a are placed into engagement with the indicator coating layers 74 of the individual indicator units 73. Prior to downward movement of the indicator ring 72, an inner circular label 66 (see FIG. 2) is removed. It is noted that prior to moving the indicator ring 72 downwardly into place, the device 70 has been incubated for three hours at the 37° C. temperature. After the indicator ring 72 is in its proper position, as shown in FIG. 11, the individual indicator units 73 may be read in approximately fifteen minutes. Again, the operator will note on an outer circular label 67a any positive test reports. The primary care physician may now prescribe a specific antibiotic.

Figure 12:
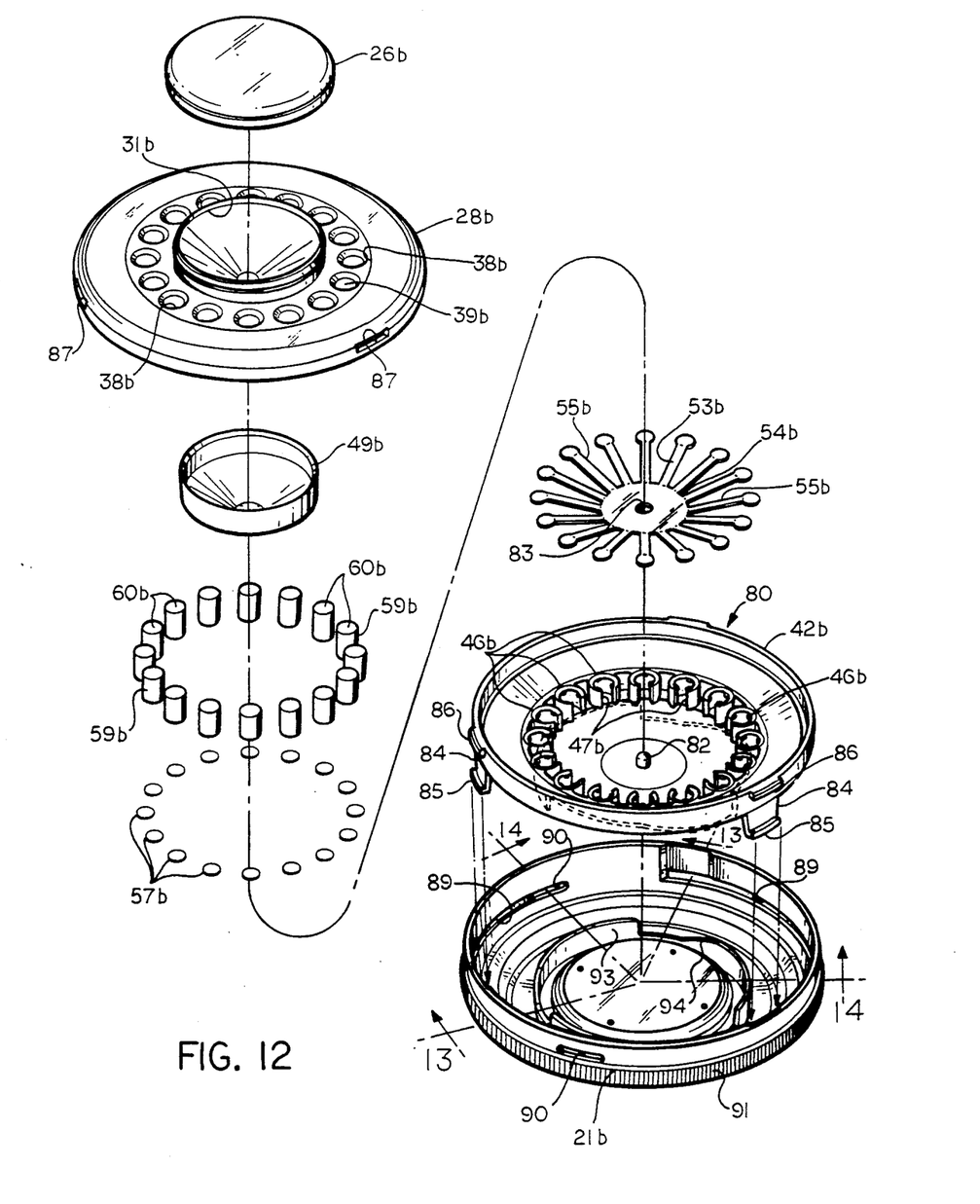
FIG. 12 is an exploded perspective view of another preferred embodiment of a diagnostic testing device, according to the present invention.
Figure 13:
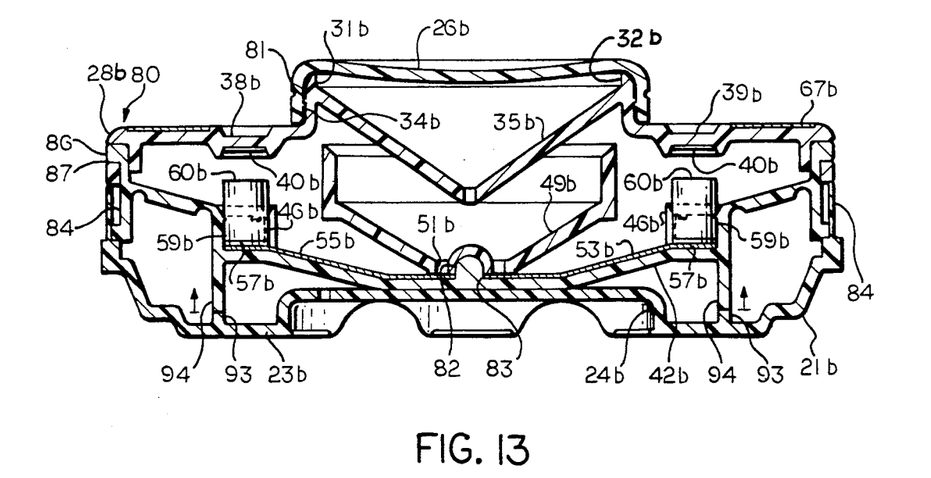
FIG. 13 is an enlarged cross-sectional view taken generally along the line 13—13 of FIG. 12.
Figure 14:
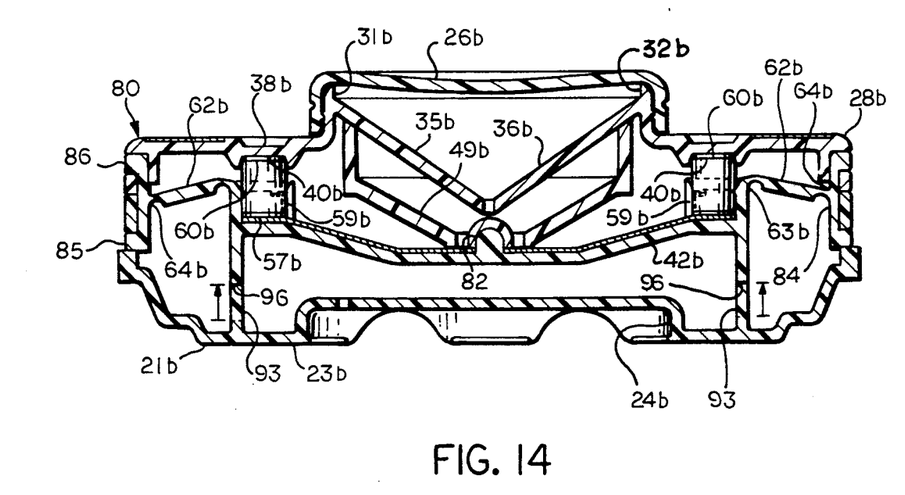
FIG. 14 is a view similar to FIG. 13 after the center unit has been cammed upwardly, taken generally along the line 14—14 of FIG. 12.

Referring to FIGS. 12-14, still another preferred embodiment of the present invention is shown. A diagnostic testing device 80 includes a base member 21b, a cover member 28b and an intermediate central member 42b. The cover member 28b defines a central opening 31b which is defined by an upwardly standing neck 32b. A cap 26b includes an inner cap ridge 34b (see FIG. 13) which snaps below a neck ridge 81 provided on the exterior of the neck 32b to lock the cap in place after the liquid specimen is placed in the testing device 80. A delivery throat 35b extends downwardly from the neck 32b and delivers the specimen to a delivery tube or funnel member 49b. The funnel member 49b has a lower end 51b which surrounds an upward center projection 82 which is defined by the central member 42b. A distribution wheel 53b is constructed of a wicking material and has a snowflake design, as shown in FIG. 12. The distribution wheel 53b defines a center opening 83 which fits over the center projection 82. The central portion 54b of the wheel 53b is positioned adjacent the lower end 51b of the funnel member 49b. The legs 55b extend radially outwardly and are received in slotted openings 47b of a plurality of circumferentially spaced antibiotic units 46b.

Antibiotic disks 57b are positioned within the antibiotic units 46b above the outer ends of the legs 55b of the distribution wheel 53b. Cylindrical delivery members 59b are positioned within the antibiotic units 46b adjacent the antibiotic disks 57b. The cylindrical delivery members 59b extend upwardly and have upper ends 60b.

The cover member 28b defines a plurality of circumferentially spaced indicator stations 38b having transparent bottoms 39b and indicator coating layers 40b on their lower surfaces. An outer circular label 67b is positioned adjacent the indicator stations 38b.

A plurality of depending tabs 84 are integrally connected at the periphery of the central member 42b and include lower end portions 85. Integral upper projections 86 are mounted above each of the end portions 85. The cover member 28b defines side slots 87 which receive the upper projections 86 upon assembly.

Referring to FIG. 12, the base member 21b defines a plurality of generally horizontal guide or side slots 89 in its interior sidewall. Each of the side slots 89 terminates in a locking recess 90. The exterior of the base member 21b, in the present embodiment, defines a circular knurled grasping ring 91. During assembly, the end portions 85 of the depending tabs 84 on the central member 42b are positioned and are movable within the side slots 89 defined by the base member 21b. When rotation is completed, as discussed below, the end portions 85 are received in the locking recesses 90.

Referring to FIGS. 13 and 14, a first edge 63b of a hinge assembly 62b is connected to the central member 42b adjacent the antibiotic units 46b. An outermost edge 64b is integrally connected to the depending tabs 84 which in turn are interconnected with the cover member 28b.

In the present embodiment, the hinge assembly 62b is a living hinge and when an overcenter position is reached, during relative vertical movement between the central member 42b and the cover member 28b, the hinge assembly 62b urges the cylindral delivery members 59b and their upper ends 60b into a positive engagement with the indicator coating layers 40b positioned on the lower surfaces of the indicator stations 38b.

In the present preferred embodiment, the diagnostic testing device 80 includes camming means for urging the central member 42b uniformly upwardly. While many types of camming means may be utilized, the present embodiment includes a plurality of upstanding cams 93 which extend upwardly from the bottom of the base member 21b. The cams 93 have ramped upper surfaces 94 which engage depending cam followers 96. The followers 96 depend from the lower surface of the central member 42b and are in a cooperating relationship with the cams 93. Referring to FIGS. 13 and 14, FIG. 13 shows the components in their lower position.

When the base member 21b is rotated relative to the cover member 28b, by rotating the grasping ring 91, the ramped upper surfaces 94 of the cams 93 engage the cam followers 96 defined on the central member 42b. Further rotation urges the central member 42b uniformly upwardly until it reaches the "up" position as shown in FIG. 14 where the living hinge 62b has urged the upper ends 60b of the cylindrical delivery member 69b into a correct engaging relationship.

When rotation is completed, the end portions 85 on the depending tabs 84 reach the end of their travel in the side slots 89 and are received in the locking recesses 90 to hold the components of the diagnostic testing device 80 in the up position, shown in FIG. 14.

During use of the diagnostic testing device 80, the cap 26b is initially positioned in a circular recess 24b defined in the lower surface 23b of the base member 21b. As is true with the earlier embodiments, a liquid specimen, such as a urine specimen, is introduced through the central opening 31b where it travels downwardly to the lower end 51b of the funnel member 49b and is directed to the distribution wheel 53b. The specimen is then distributed evenly and moves outwardly to the antibiotic units 46b. At that time, the cap 26b is removed from the base member 21b and snapped in place over the neck 32b of the cover member 28b, as shown in FIGS. 13 and 14. The diagnostic testing device 80 is then inverted and incubated for a three hour period at the 37° C. temperature. After incubation the ring 91 is grasped and rotated moving the cylindrical delivery members 59b upwardly until the ends 60b are in engagement with the respective indicator coating layers 40b. After a fifteen minute time period, the operator views the respective indicator stations 38b and notes any positive results on the outer circular label 67b. The label is then removed and placed in the patient file.

With this information, the primary care physician is able to prescribe a specific antibiotic for the patient.

Numerous revisions and changes may be made to the disclosed embodiments of the invention without departing from the scope of the following claims.

We claim:

1. A diagnostic testing device comprising, in combination, a base member defining a cavity, a plurality of antibiotic units within said cavity;

a cover member on said base member, said cover member defining a central cover opening for the reception of a liquid specimen;

a central member positioned between said base member and said cover member, said central member having said plurality of antibiotic units spaced inwardly from its periphery;

distribution means comprising a porous wicking material positioned between said cover opening and said antibiotic units for delivering portions of the liquid specimen to said antibiotic units, said distribution means including a fibrous distribution wheel having a central portion and a plurality of legs extending outwardly from said central portion, said fibrous distribution wheel being positioned on said central member, the outer ends of each of said legs received by a respective one of said antibiotic units;

indicator means in communication with said cover member for indicating the effectiveness of antibiotics;

delivery means comprising a porous wicking material extending upwardly from each of said antibiotic units, whereby relative vertical movement between said delivery means and said indicator means places said delivery means and said indicator means into an engaging relationship, said delivery means including a fibrous cylinder positioned in each of said antibiotic units and extending upwardly toward said cover member; and means for stably biasing said cover member and said central member in first and second positions relative to each other whereby in said first position said fluid delivery means and indicator means are not in fluid communication with each other and in said second position said fluid delivery means and indicator means are in fluid communication with each other.

2. A diagnostic testing device, according to claim 1, wherein said cover member defines a plurality of indicator stations complementary with said delivery means.

3. A diagnostic testing device, according to claim 1, wherein said distribution means includes a funnel member having an upper end and a lower end.

4. A diagnostic testing device according to claim 1, wherein said distribution means includes a distribution wheel having a central portion and a plurality of legs extending outwardly from said central portion to said antibiotic units.

5. A diagnostic testing device, according to claim 1, wherein each of said antibiotic units comprising a cylindrical member extending upwardly from said central member, said cylindrical antibiotic unit holding an antibiotic disk.

6. A diagnostic testing device, according to claim 1, including a cap for closing said central cover opening in said cover member.

7. A diagnostic testing device, according to claim 6, wherein said cover member defines a neck surrounding said central cover opening, said neck and said cap having locking means for securing said cap to said cover member after said cap is positioned on said neck.

8. A diagnostic testing device, according to claim 6, wherein said base member has a lower surface, such lower surface containing a circular recess, said cap and said circular recess having retaining means for initially holding said cap in said circular recess.

9. A diagnostic testing device, according to claim 1, including hinge means attached to said central member, whereby upward movement of said base member urges said delivery means into engagement with said indicator means.

10. A diagnostic testing device, according to claim 9, wherein said hinge means comprises a living hinge integrally attached at the periphery of said central member and having its outermost edge positioned adjacent said cover member.

11. A diagnostic testing device, according to claim 9, including a tear strip positioned between said cover member and said base member, wherein removal of said tear strip allows relative vertical movement between said cover member and said base member.

12. A diagnostic testing device, according to claim 1, including cam means between said base member and said central member for urging said central member uniformly upwardly relative to said cover member.

13. A diagnostic testing device, according to claim 12, wherein said cam means includes upwardly extending cam members positioned on said base member and cam followers extending downwardly from said central member, whereby rotation of said base member and the resultant movement of the cam members relative to said cam followers urges said central member uniformly upwardly toward said cover member.

14. A diagnostic testing device, according to claim 13, said base member including a circular sidewall, a plurality of slots defined in said sidewall of said base member, a plurality of depending tabs mounted on said central member, said depending tabs having end portions received by said slots, said base member defining locking recesses adjacent the ends of said slots, wherein when said central member is moved by said cam means to said second position, said end portions of said depending tabs are received in said locking recesses.

15. A diagnostic testing device comprising, in combination,
    a base member defining a cavity, a central member positioned in said cavity, a plurality of antibiotic units spaced inwardly from the periphery of said center member, each of said antibiotic units including a generally cylindrical member extending upwardly from said central member, said cylindrical member receiving an antibiotic disk;
    a cover member on said base member, said cover member defining a central cover opening for the reception of a liquid specimen;
    distribution means comprising a porous wicking material positioned between said cover opening and said antibiotic units, said distribution means including a liquid supply conduit extending downwardly from said cover opening and a fibrous distribution member having a central portion in liquid communication with said supply conduit and a plurality of liquid transmission legs extending outwardly from said central portion to said antibiotic units, said fibrous distribution member being positioned on said central member, the outer ends of each of said legs being received by a respective one of said cylindrical members, an antiobiotic disk engaging said cylindrical member adjacent such outer end of said leg;
    indicator means in communication with said cover for indicating the effectiveness of antibiotics, wherein said indicator means includes a plurality of indicator stations defined by said cover member;
    delivery means including a fibrous cylinder of a porous wicking material positioned in each of said cylindrical members and extending upwardly from each of said antibiotic units toward said cover member, whereby relative vertical movement between said delivery means and said indicator means places said delivery means and said indicator means into an engaging relationship and;
    means for stably biasing said cover member and said central member in first and second positions relative to each other whereby in said first position said fluid delivery means and indicator means are not in fluid communication with each other and in said second position said fluid delivery means and indicator means are in fluid communication with each other.

16. A diagnostic testing device, according to claim 15, including hinge means positioned between said central member and said cover member, whereby upward movement of said base member urges said delivery means into engagement with said indicator means.

17. A diagnostic testing device, according to claim 16, wherein said hinge means comprises a living hinge integrally attached at the periphery of said central member and having its outermost edge positioned adjacent said cover member.

18. A diagnostic testing device, according to claim 16, including a tear strip positioned between said cover member and said base member, wherein removal of said tear strip allows relative vertical movement between said cover member and said base member.

19. A diagnostic testing device comprising, in combination,
    a base member defining a cavity, a central member positioned in said cavity, a plurality of antibiotic units on said central member;
    a cover member on said base member, said cover member defining a central cover opening for the reception of a liquid specimen;
    distribution means comprising a porous wicking material positioned between said cover opening and said antibiotic units for delivering portions of the liquid specimen to said antibiotic units;
    indicator means in communication with said cover for indicating the effectiveness of antibiotics;
    delivery means comprising a porous wicking material extending upwardly from each of said antibiotic units, whereby relative vertical movement between said delivery means and said indicator means places said delivery means and said indicator means into an engaging relationship and;
    means for stably biasing said cover member and said central member in first and second positions relative to each other whereby in said first position said fluid delivery means and indicator means are not in fluid communication with each other and in said second position said fluid delivery means and indicator means are in fluid communication with each other.

20. A diagnostic testing device, according to claim 19, wherein said indicator means includes a plurality of indicator stations defined by said cover member.

21. A diagnostic testing device, according to claim 19, wherein said distribution means includes a fibrous distribution wheel having a central portion and a plurality of legs extending outwardly from said central portion to said antibiotic units.

22. A diagnostic testing device, according to claim 21, wherein each of said antibiotic units includes a cylindrical member extending upwardly from said central member, said cylindrical member receiving an antibiotic disk.

23. A diagnostic testing device, according to claim 22, wherein said fibrous distribution wheel is positioned on said central member, the outer ends of each of said legs being received by a respective one of said cylindrical members, an antibiotic disk engaging said cylindrical member adjacent the outer end of the leg, said delivery means including a fibrous cylinder positioned in each of said cylindrical members and extending upwardly toward said cover member.

24. A diagnostic testing device, according to claim 19, including a tear strip positioned between said cover member and said base member, wherein removal of said tear strip allows relative vertical movement between said cover member and said base member.

25. A diagnostic testing device, according to claim 19, including cam means between said base member and said central member for urging said center member uniformly upwardly relative to said cover member.

26. A diagnostic testing device, according to claim 25, wherein said cam means includes upwardly extending cam members positioned on said base member and cam followers extending downwardly from said central member, whereby rotation of said base member and the resultant movement of the cam members relative to said cam followers urges said central member uniformly upwardly toward said cover member.

27. A diagnostic testing device, according to claim 26, said base member including a circular sidewall, a plurality of slots defined in said sidewall of said sidewall, a plurality of depending tabs mounted on said central member, said depending tabs having end portions received by said slots, said base member defining locking recesses adjacent the ends of said slots, wherein when said central member is moved by said cam means to said second position, said end portions of said depending tabs are positioned in said locking recesses.

* * * * *